tion No. PCT/EP2004/

(12) United States Patent
Weide et al.

(10) Patent No.: US 7,557,145 B2
(45) Date of Patent: Jul. 7, 2009

(54) INHIBITION OF THE ASEXUAL REPRODUCTION OF FUNGI BY EUGENOL AND/OR DERIVATIVES THEREOF

(75) Inventors: Mirko Weide, Duesseldorf (DE); Anja Schloesser, Neuss (DE); Dirk Bockmuehl, Wuppertal (DE); Andreas Bolte, Duesseldorf (DE); Roland Breves, Mettmann (DE)

(73) Assignee: Henkel Kommanditgesellschaft auf Aktien (Henkel KGAA), Duesseldorf (DE)

( * ) Notice: Subject to any disclaimer, the term of this patent is extended or adjusted under 35 U.S.C. 154(b) by 217 days.

(21) Appl. No.: 11/305,380

(22) Filed: Dec. 16, 2005

(65) Prior Publication Data

US 2006/0128813 A1    Jun. 15, 2006

Related U.S. Application Data

(63) Continuation of application No. PCT/EP2004/006289, filed on Jun. 11, 2004.

(30) Foreign Application Priority Data

Jun. 17, 2003   (DE) ................. 103 27 136
Jun. 17, 2003   (DE) ................. 103 27 137

(51) Int. Cl.
  *A61K 31/075*   (2006.01)
  *C07C 43/20*    (2006.01)
(52) U.S. Cl. ....................... 514/718; 568/654
(58) Field of Classification Search ............ 514/718; 568/654
  See application file for complete search history.

(56) References Cited

U.S. PATENT DOCUMENTS

| | | | |
|---|---|---|---|
| 3,234,258 A | 2/1966 | Morris | 558/42 |
| 3,547,828 A | 12/1970 | Mansfield | 516/72 |
| 3,595,975 A | 7/1971 | Gauvreau | 514/179 |
| 3,707,535 A | 12/1972 | Lew | 536/18.6 |
| 3,772,269 A | 11/1973 | Lew | 536/4.1 |
| 3,839,318 A | 10/1974 | Mansfield | 536/18.6 |
| 4,349,669 A | 9/1982 | Klahr et al. | 536/127 |
| 4,417,042 A | 11/1983 | Dziark | 528/18 |
| 4,477,361 A | 10/1984 | Sperti et al. | 510/131 |
| 4,503,210 A | 3/1985 | Von Au | 528/33 |
| 4,664,839 A | 5/1987 | Rieck | 252/175 |
| 4,715,408 A | 12/1987 | Eisenlohr | 139/54 |
| 4,717,260 A | 1/1988 | Tsuji | 368/21 |
| 4,820,439 A | 4/1989 | Rieck | 510/469 |
| 4,891,400 A | 1/1990 | Schwabe et al. | 524/745 |
| 4,910,242 A | 3/1990 | Podola et al. | 524/158 |
| 4,912,153 A | 3/1990 | Jeremias et al. | 524/731 |
| 4,942,211 A | 7/1990 | Sommer et al. | 528/14 |
| 5,075,041 A | 12/1991 | Lutz | 510/537 |
| 5,077,360 A | 12/1991 | DePompei et al. | 526/217 |
| 5,356,607 A | 10/1994 | Just | 423/334 |
| 5,412,015 A | 5/1995 | Sommer et al. | 524/425 |
| 5,502,144 A | 3/1996 | Kuo et al. | 528/18 |
| 5,525,654 A | 6/1996 | Podola et al. | 524/199 |
| 5,529,779 A | 6/1996 | Hamada et al. | 424/539 |
| 5,614,484 A | 3/1997 | Panandiker | 510/102 |
| 5,646,197 A * | 7/1997 | Martin | 523/118 |
| 5,679,351 A | 10/1997 | Walter et al. | 424/725 |
| 5,705,169 A | 1/1998 | Stein et al. | 424/401 |
| 5,730,960 A | 3/1998 | Stein et al. | 424/59 |
| 5,780,420 A | 7/1998 | Breuer et al. | 510/466 |
| 5,880,299 A | 3/1999 | Obiols et al. | 554/109 |
| 5,929,124 A | 7/1999 | Hostettmann et al. | 514/691 |
| 5,945,091 A | 8/1999 | Habeck et al. | 424/59 |
| 6,071,867 A | 6/2000 | Purcell et al. | 510/174 |
| 6,139,866 A * | 10/2000 | Chono et al. | 424/443 |
| 6,153,227 A | 11/2000 | Shibuya et al. | 424/539 |
| 6,184,274 B1 | 2/2001 | Herold et al. | 524/114 |
| 6,193,960 B1 | 2/2001 | Metzger et al. | 424/59 |
| 6,241,975 B1 | 6/2001 | Moon et al. | 424/58 |
| 6,271,267 B1 | 8/2001 | Matsuoka et al. | 514/739 |
| 6,486,333 B1 | 11/2002 | Murayama et al. | 554/52 |
| 2002/0177621 A1 | 11/2002 | Hanada et al. | 514/461 |
| 2003/0180349 A1 | 9/2003 | Franklin | 424/450 |
| 2004/0266634 A1 | 12/2004 | Bockmuhl et al. | 510/101 |
| 2005/0009929 A1 | 1/2005 | Bockmuhl et al. | 514/729 |
| 2006/0130702 A1 | 6/2006 | Weide et al. | 510/101 |
| 2006/0134239 A1 | 6/2006 | Weide et al. | 424/725 |

FOREIGN PATENT DOCUMENTS

| | | |
|---|---|---|
| CA | 2078787 | 9/1991 |
| CA | 1 294 724 | 1/1992 |
| CH | 688787 A | 3/1998 |
| DE | 1 165 574 B | 3/1964 |
| DE | 1943689 A1 | 3/1970 |
| DE | 2036472 A1 | 2/1971 |
| DE | 3001064 A1 | 7/1981 |
| DE | 2024051 C3 | 5/1986 |
| DE | 3602526 A1 | 7/1987 |
| DE | 3726547 A1 | 2/1989 |
| DE | 4009095 A1 | 9/1991 |

(Continued)

OTHER PUBLICATIONS

U.S. Appl. No. 11/303,630, filed Dec. 16, 2005, Weide et al.

(Continued)

*Primary Examiner*—Paul A Zucker
(74) *Attorney, Agent, or Firm*—Woodcock Washburn LLP

(57) ABSTRACT

This invention relates to the use of eugenol and/or eugenol derivatives for inhibiting the asexual propagation of fungi. This invention also relates to filter media, adhesives, building materials, building auxiliaries, textiles, pelts, paper, skins or leather, laundry detergents, cleaning compositions, rinse agents, hand washing preparations, manual dishwashing detergents, machine dishwashing detergents and preparations for finishing building materials, building auxiliaries, textiles, pelts, paper, skins or leather that contain eugenol and/or eugenol derivatives and to preparations for treating building materials, building auxiliaries, textiles, pelts, paper, skins or leather that contain eugenol and/or eugenol derivatives.

14 Claims, No Drawings

FOREIGN PATENT DOCUMENTS

| | | |
|---|---|---|
| DE | 4029504 A1 | 3/1992 |
| DE | 4233077 A1 | 4/1994 |
| DE | 44 00 024 A1 | 7/1995 |
| DE | 19539846 C1 | 11/1996 |
| DE | 195 23 320 A1 | 1/1997 |
| DE | 19549425 A1 | 3/1997 |
| DE | 19704553 A1 | 8/1998 |
| DE | 19712033 A1 | 9/1998 |
| EP | 0 118 030 A1 | 9/1984 |
| EP | 0 077 167 B1 | 9/1985 |
| EP | 0 214 306 A1 | 3/1987 |
| EP | 0 164 514 B1 | 6/1989 |
| EP | 0 214 322 B1 | 12/1989 |
| EP | 0 214 293 B1 | 7/1990 |
| EP | 0 451 889 A1 | 10/1991 |
| EP | 0 316 591 B1 | 12/1993 |
| EP | 0 327 847 B1 | 1/1994 |
| EP | 0 553 143 B1 | 5/1995 |
| EP | 0 703 292 B1 | 3/1996 |
| EP | 0 728 749 B1 | 8/1996 |
| EP | 0 693 471 B1 | 1/1998 |
| EP | 0 694 521 B1 | 1/1998 |
| EP | 0 818 450 A1 | 1/1998 |
| EP | 1 044 685 A2 | 10/2000 |
| EP | 1 059 032 A1 | 12/2000 |
| EP | 1 238 650 A2 | 9/2002 |
| EP | 1 094 065 B1 | 12/2003 |
| FR | 2 252 840 A1 | 6/1975 |
| GB | 962919 | 7/1964 |
| GB | 1333475 | 10/1973 |
| GB | 1494915 | 12/1977 |
| JP | 53-091123 | 8/1978 |
| JP | 56-73002 | 6/1981 |
| JP | 10-17483 | 1/1998 |
| JP | 2003-012411 * | 1/2003 |
| WO | 91/08171 A1 | 6/1991 |
| WO | 95/07331 A1 | 3/1995 |
| WO | 96/32953 A1 | 10/1996 |
| WO | 97/07193 A1 | 2/1997 |
| WO | 97/30689 A1 | 8/1997 |
| WO | 97/45511 A1 | 12/1997 |
| WO | 98/02044 A1 | 1/1998 |
| WO | 98/25638 A1 | 6/1998 |
| WO | 99/09824 A1 | 3/1999 |
| WO | 00/27981 A1 | 5/2000 |
| WO | 00/67726 | 11/2000 |
| WO | 00/68232 A1 | 11/2000 |
| WO | 01/09249 A1 | 2/2001 |
| WO | 01/24769 A1 | 4/2001 |
| WO | 01/79409 A1 | 10/2001 |
| WO | 02/47615 A2 | 6/2002 |
| WO | 03/018042 A1 | 3/2003 |
| WO | 03/051124 A2 | 6/2003 |
| WO | 03/051126 A1 | 6/2003 |
| WO | 2004/054561 A1 | 7/2004 |
| WO | 2004/110147 | 12/2004 |

OTHER PUBLICATIONS

U.s. Appl. No. 11/305,364, filed Dec. 16, 2005, Bockmuhl et al.
DSMZ—List of Filamentous Fungi; Available on the world wide web at dsmz.de/species/fungi.htm.
DSMZ—List of Yeasts Available on the world wide web at dsmz.de/species/yeasts.htm.
Ullmann's Encyclopedia of Industrial Chemistry 6$^{th}$ Edition 2003, Chapter 4.
Ullmann's Encyclopedia of Industrial Chemistry, Chapter 4, vol. 20, Verlag Chemie GmbH, Weinheim, 1981, p. 276—carnation oil.
CTFA Cosmetic Ingredient Dictionary, The Cosmetic, Toiletry and Fragrance Association, Inc., 1997.
Finkel, P., SÖFW-Journal 122, 543-548, 1996.
Morris, J. A. et al., "Antimicrobial activity of aroma chemicals and essential oils," *J. Am. Oil Chem. Soc.*, 1979, 56, 595-603.
Hagers Handbuch d. Pharmazeutischen Praxis, Chapter 5, vol. 6, Drugs P-Z, Springer Verlag Berlin, 1994, pp. 858-864—carnation oil.
Database Biosis Accession No. PREV198579104006; Nava-Rodriguez, V. M. T. et al., "Effect of Different Chemicals on the Development of Several Molds from Stored Grains," *Boletin de la Sociedad Mexicana de Micologia*, 1983, 18, 85-94, XP002297854.
Database Biosis Accession No. PREV1998376031974; Boonchird, C. et al., "In-Vitro Anti Fungal Activity of Eugenol and Vanillin Against Candida-Albicans and Cryptococcus-Neoformans," *Canadian Journal of Microbiology*, 1982, 11, 1235-1241, XP00297855.
Database Biosis Accession No. PREV198580067051, Al-Khayat, M. A. et al., "Phenolic Spice Components Sporostatic to Bacillus-Subtilis," *Journal of Food Science*, 1985, 50(4), 971-974, XP002297856.
Aldrich Chemical Company catalog, 1994-1995, p. 694, Aldrich Chemical Company, Milwaukee, WI, 1994, no month available.
Appendix 6, Parts A and B of the Kosmetikverordnung ("Cosmetics Directive").
Cajkovac et al., "Wirkungantimikorbieller Mittel auf Candida in der Zahnpasta", Parfumerie und Kosmetik, vol. 71, pp. 786-791 (1990) [English summary included on pp. 790-792].
Hornby et al., "Quorum Sensing in the Dimorphic Fung Canadida albicans Is Mediated by Farnesol", Applied and Environmental Microbiology, pp. 2982-2992, vol. 67. No. 1 (Jul. 2001).
"Kosmetische Färbemittel" of the Farbstoffkommission der Deutschen Forschungsgemeinschaft, Verlag Chemie, Weinheim, 1984, pp. 81 to 106.
Paster, B. J. et al., "Bacterial Diversity in Human Subgingival Plaque," Journal of Bacteriology, Jun. 2001 183(12), 3770-3783.
Pattnaik et al., "Antibacterial and antifungal activity of ten essential oils in vitro," (Microbios), vol. 86, No. 439, Abstract only.
CA139: 210663.
CA132: 293276.
CA133: 117308.
CA125: 296936.
CAPLUS abstract: Abe, S. et al., "Anticandida albicans activity of essential oils including lemongrass (Cymbopogon citrates) oil and its component, citral," *Nippon Ishinkin Gakkai Zasshi*, 44(4), 2003, 285-291, XP002294229.
Database Biosis Accession No. PREV200300226998, Vilas, A. et al., "Effect of reaction parameters on synthesis of citronellyl methacrylate by lipase-catalyzed transesterification," *Biotechnology Progress*, 2003, 19(2), 298-302.
Database Biosis Accession No. PREV199698770831, Muneo, T. et al., "2-Hydroxypropylated cyclodextrins as a sustained-release carrier for fragrance materials," *Chemical and Pharmaceutical Bulletin*(Tokyo), 1996, 44(2), 416-420.
Database Biosis Accession No. PREV199799813213, Ananthan, K. et al., "Cyclodextrin complexed flavors retention in extruded starches," *Journal of Food Science*, 1997, 62(5), 1057-1060.
Derwent Abstract, JP 2001-002542, Jan. 9, 2001, XP-002294230.
Derwent Abastract, JP 3-167132, Jul. 19,1991, XP-0022942321.
Derwent Abastract, JP 6-016517, Jan. 25, 1949, XP-002294232.
WPI/Derwent Abstract: JP2003012411, Jan. 15, 2003, XP002297973.
Patent Abstracts of Japan, vol. 1999, No. 3, JP10338630, Dec. 22, 1998.
Patent Abstracts of Japan for JP 10-017484 (Jan. 20, 1998).
Patent Abstracts of Japan for JP 10-017483 (Jan. 20, 1998).
Abstract XP002235743 of JP 53-091123 "Fungicide for Textiles, cosmetics, paper, plastics,etc. -contains farnesol as active ingredient, having antibiotic activity on gram-positive bacteria".
Patent Abstracts of Japan for JP 56-073002 (1981).
Parfümerie und Kosmetik, 80. Jahrgang, Nr. 3/99, p. 11, (1999).
R. Lochhead *Cosm. Toil.* 108, 95-138 (1993).
T. Belaiche et al., Etude De L'Influence Des Terpenes Sur La Sporulation D'Aspergilla Industries Alimentaires & Agricoles, vol. 116, XP009007965, pp. 27-29 (1999) [English summary included].

Todd, C. et al. "Volatile silicone fluids for cosmetic formulations," in *Cosm. Toil.* 91, 29-32 (1976).

Ullmann's Encyklopadie d. tech. Chemie, 4. Aufl., Band 20, Verlag Chemie, Weinheim u.a. 1981, 277.

Vallejo, I. et al., "Differential behaviour or mycelial growth of several Botrytis cinerea strains on either patchoulol- or Globulol-amended media," *J. Phytopathology*, 2001, 149, 113-118.

V. G. Billerbeck et al., "Effects of Cymbopogon nardus (L.) W. Watson essential oil on the growth and morphogenesis of Aspergillus niger," Can. J. Microbiol., vol. 47, pp. 9-17 (2001).

Yang, D. et al., "Proprietes antifongiques et antibacteriennes, in vitro, de trios huiles essentielles de Patchouli d'origine differentes," *Acta Bot. Gallica*, 143(1), 1996, 29-35.

* cited by examiner

INHIBITION OF THE ASEXUAL REPRODUCTION OF FUNGI BY EUGENOL AND/OR DERIVATIVES THEREOF

CROSS REFERENCE TO RELATED APPLICATIONS

This application is a continuation of PCT/EP2004/006289, filed Jun. 11, 2004, which claims priority to DE 103 27 136.8, filed Jun. 17, 2003 and DE 103 27 137.6, filed Jun. 17, 2003, the disclosures of each of which are incorporated herein in their entireties.

Fungi and especially molds cause serious problems in the field of building biology because the spores which they release into the air are often allergenic. Combating such fungi with biocides often involves an increased risk of resistance buildup so that, after a time, new antimicrobial agents have to be found to act against the now resistant microorganisms. Moreover, biocides are not always ecologically and toxicologically safe. Unwanted effects of the spread of molds include, in particular, discoloration (for example on walls, jointing compounds and other bathroom surfaces) which is caused by pigmented spores.

Delicate textiles, such as silk or microfibers for example, are being increasingly made up into articles of clothing which can only be washed at 30 or 40° C. However, fungi such as, for example, the human-pathogenic *Candida albicans* are not destroyed at those temperatures. After a fungal infection in particular, these fungi—which adhere to articles of clothing—can lead to re-infection.

Accordingly, antimicrobial agents which either inhibit the growth of the fungi (fungistatic agents) or destroy them (fungicides) have hitherto been used. The antimicrobial agents used for this purpose are often non-selective, i.e. act both against bacteria and against fungi. The disadvantage of this is that corresponding biocides or biostatics used, for example, in laundry detergents and cleaners pollute the wastewater and hence also functionally impair the microbial stages of wastewater treatment plants.

It is known from the prior art that eugenol used in high concentrations is suitable for inhibiting the growth of fungi (fungistatic effect) or even for destroying the fungi (fungicidal effect). It is not mentioned in the prior art that eugenol can be used for inhibiting the asexual propagation of fungi (especially sporulation). Naturally, general growth inhibition also results in the inhibition of asexual propagation, especially sporulation. It is not known from the prior art that eugenol reduces and/or completely prevents or can inhibit the asexual propagation of fungi, especially sporulation, without inhibiting the growth of the fungi per se.

According to earlier, hitherto unpublished International Patent Application PCT/EP02/14306, mono-, sesqui- and/or diterpenes and derivatives thereof can be used for inhibiting the asexual propagation of fungi. Farnesol is mentioned as a particularly preferred active component. The use of eugenol for inhibiting the asexual propagation of fungi is not mentioned in that application.

Accordingly, the problem addressed by the present invention was to overcome the disadvantages of the prior art and to prevent the asexual propagation of fungi, more particularly the sporulation of molds, particularly on surfaces It has surprisingly been found that the use of eugenol and/or eugenol derivatives on or in materials infested by fungi suppresses the spread of the fungi without actually destroying them.

Accordingly, the present invention relates to the use of eugenol and/or eugenol derivatives for inhibiting the asexual propagation of fungi.

In the context of the invention, the term "asexual propagation" encompasses in particular sporulation, budding and fragmentation.

Eugenol in the context of the invention is understood to be 4-allyl-2-methoxyphenol. Eugenol derivatives preferably include esters and ethers of eugenol which are formed by reaction with the phenolic hydroxyl group, more particularly eugenol ethers, eugenol benzoate, eugenol palmitate, eugenol cinnamate and eugenol acetate (acetoeugenol). Eugenol-O-β-D-glucopyranoside (citrusin C) is also suitable. Eugenol is particularly preferred.

Esters of eugenol with silicic acids corresponding to formulae I and II are also suitable. The eugenol silicic acid esters are produced, in particular, by simple transesterification of silicid acid esters (n=1) or oligosilicic acid esters (n>1) of lower alcohols with eugenol (or optionally mixtures of eugenol with other alcohols, more particularly terpene alcohols). Depending on the reaction time and reaction conditions, the lower alcohols are eliminated and the eugenol is bound, the alcohols along the Si—O—Si chain being exchanged more easily than the terminal alcohols.

A particularly preferred embodiment is characterized by the use of eugenol silicic acid esters corresponding to either of formulae (I) or (II) and/or mixtures thereof:

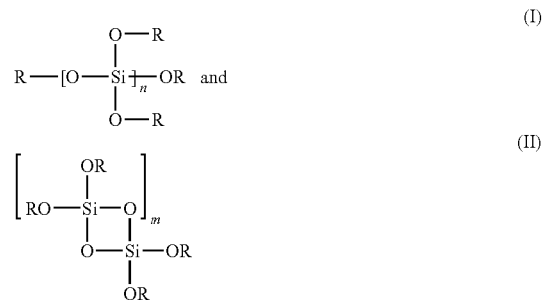

in which at least one R is eugenyl (4-allyl-2-methoxyphenyl) and all other Rs independently of one another are selected from the group consisting of H, linear or branched, saturated or unsaturated, substituted or unsubstituted $C_{1-6}$ hydrocarbon residues, terpene alcohols and polymers, m has a value of 1 to 20 and n has a value of 1 to 100.

In another preferred embodiment, at least two or three substituents R are eugenyl (=4-allyl-2-methoxyphenyl).

The degrees of oligomerization "n" of the silicic acid esters according to the invention are between 1 and 20. In preferred compounds, n has a value of 1 to 15, preferably 1 to 12 and more particularly 1 to 10, the values 4, 5, 6, 7 and 8 being most particularly preferred.

Advantageously, the fungi are neither growth-inhibited nor destroyed by the use according to the invention; their asexual propagation is merely inhibited or suppressed. The selection pressure for the buildup of resistances is therefore minimal.

It has surprisingly been found that the use of eugenol and/or derivatives thereof can inhibit the asexual propagation of fungi better, i.e. in a lower concentration, than farnesol.

Another advantage of the invention is that, compared with fungicides or fungistatic agents, eugenol and/or eugenol derivatives are active in low final concentrations so that there is little risk of unwanted side effects.

In a preferred embodiment of the present invention, eugenol and/or eugenol derivatives are used to inhibit sporulation. Sporulation in the present context is understood to be the formation both of propagation forms, for example conidiae, gonitocysts, sporangiospores, arthrospores, blastospores and their associated organs (for example conidiophores), and of permanent forms (for example chlamydospores).

Since mold spores are ubiquitously present in room air, mold infestation cannot basically be prevented. However, inhibiting the sporulation of growing fungal colonies enables the risk of a mold allergy to be considerably reduced and the spread of the fungus to be completely stopped or significantly delayed. Discoloration through sporulation is also greatly reduced or completely prevented.

The use of eugenol and/or eugenol derivatives for inhibiting sporulation has the further advantage that, surprisingly, the concentration required for inhibiting sporulation is considerably lower by comparison with other sesquiterpenes, for example farnesol. Thus, a comparable effect can even be achieved with a lower concentration of active component.

In addition, eugenol has a clove-like perfume which can provide the corresponding substances/preparations/products according to the invention with a pleasant perfume note and may even eliminate the need to add more perfume.

In one particular embodiment, eugenol and/or eugenol derivatives are used in final concentrations which are not fungicidal (i.e. do not destroy fungi) or fungistatic (i.e. do not inhibit the growth of fungi). One particular advantage of this embodiment is that the risk of resistance to the substances used being built up is fairly minimal because the fungi are neither destroyed nor growth-inhibited. These minimum inhibiting concentrations may readily be determined in known manner.

In another particular embodiment, eugenol and/or eugenol derivatives are present in concentrations of 0.000001 to 2% by weight. One particular advantage of this embodiment is that only small concentrations of these substances need be present to reduce or substantially completely prevent the asexual propagation of the fungi. Eugenol and/or eugenol derivatives are preferably present in concentrations of 0.00001 to 1% by weight and more especially in concentrations of 0.0001 to 0.1% by weight. Concentrations of 0.001 to 0.01% by weight are particularly preferred.

The concentrations which lead to the desired result in the end product are significantly lower than those mentioned because dilutions have to be taken into account for many products. For laundry detergents, a dilution factor (ratio of detergent concentrate to water) of 1:20 to 1:200, for example, can be expected. The dilution ratio for laundry detergents is often between 1:60 and 1:100, for example 1:80. In the final in-use solution, concentrations of 0.0001 to 5% by weight in particular have a particularly good sporulation-inhibiting effect. Concentrations of 0.001 to 0.1% by weight, for example 0.001% by weight, are preferably used.

For eugenol, concentrations of 0.0001 to 1.0% by weight and more especially 0.001 to 0.1% by weight would be suitable.

The effect of eugenol and/or eugenol derivatives according to the invention is particularly suitable for inhibiting the asexual propagation of all the fungi listed in the stock lists "DSMZ—List of Filamentous Fungi" and "DSMZ—List of Yeasts" of the DSMZ (Deutsche Stammsanunlung von Mikroorganismen und Zellkulturen GmbH, Braunschweig). The lists are available on the internet at the world wide web at dsmz.de/species/fungi.htm and dsmz.de/species/yeasats.htm.

The substances eugenol and/or eugenol derivatives used in accordance with the invention are particularly suitable for inhibiting the asexual propagation of fingi. Such fingi include, for example, the human-pathogenic species of the Ascomycota, Basidiomycota, Deuteromycota and Zygomycota classes, more particularly any species of the geni *Aspergillus, Penicillium, Cladosporium* and *Mucor*, the human-pathogenic forms of *Candida* and *Stachybotrys, Phoma, Alternaria, Aureobasidium, Ulocladium, Epicoccum, Stemphyllium, Paecilomyces, Trichoderma, Scopulariopsis, Wallemia, Botrytis, Verticillium* and *Chaetonium*

The Ascomycota include in particular all species of the geni *Aspergillus, Penicillium* and *Cladosporium*. These fingi form spores which have a strong allergenic potential on contact with the skin or the respiratory tract. The Basidiomycota include, for example, *Cryptococcus neoformans*. The Deuteromycota include all geni known as molds, more particularly those which cannot be assigned to the Ascomycota, Basidiomycota or Zygomycota class through the absence of a sexual stage.

The eugenol and/or eugenol derivatives usable in accordance with the invention are particularly suitable for inhibiting sporulation in all species of the genus *Aspergillus*, more particularly in species selected from *Aspergillus aculeatus, Aspergillus albus, Aspergillus alliaceus, Aspergillus asperescens, Aspergillus awamori, Aspergillus candidus, Aspergillus carbonarius, Aspergillus carneus, Aspergillus chevalieri, Aspergillus chevalieri* var. *intermedius, Aspergillus clavatus, Aspergillus ficuum, Aspergillus flavipes, Aspergillus flavus, Aspergillus foetidus, Aspergillus fumigatus, Aspergillus giganteus, Aspergillus humicola, Aspergillus intermedius, Aspergillus japonicus, Aspergillus nidulans, Aspergillus niger, Aspergillus niveus, Aspergillus ochraceus, Aspergillus oryzae, Aspergillus ostianus, Aspergillus parasiticus, Aspergillus parasiticus* var. *globosus, Aspergillus penicillioides, Aspergillus phoenicis, Aspergillus rugulosus, Aspergillus sclerotiorum, Aspergillus sojae* var. *gymnosardae, Aspergillus sydowi, Aspergillus tamarii, Aspergillus terreus, Aspergillus terricola, Aspergillus toxicarius, Aspergillus unguis, Aspergillus ustus, Aspergillus versicolor, Aspergillus vitricolae* and *Aspergillus wentii*.

In a particularly preferred embodiment, eugenol and/or eugenol derivatives are most particularly preferred for inhibiting sporulation in species of the genus *Aspergillus* selected from *Aspergillus flavus* and *Aspergillus nidulans*.

The present invention also relates to laundry detergents, cleaning compositions, rinse agents, hand washing preparations, manual dishwashing detergents, machine dishwashing detergents and compositions for treating filter media, building materials, building auxiliaries, textiles, pelts, paper, skins or leather which contain eugenol and/or eugenol derivatives for inhibiting the asexual propagation of fungi.

The present invention also relates to filter media, building materials, building auxiliaries, textiles, pelts, paper, skins or leather which contain eugenol and/or eugenol derivatives and/or which have been treated with a preparation according to the invention.

The paper, textiles, wall coverings, pelts, skins or leather is/are treated in known manner, for example by immersion in a suitably concentrated solution of a composition according to the invention.

The filter media, building materials or building auxiliaries are treated, for example, by mechanical incorporation or application of a suitably concentrated solution of a preparation according to the invention in or to the filter media, building materials or building auxiliaries. Eugenol and solutions of eugenol, preferably in organic solvents, may advantageously be applied to or incorporated particularly well in such building materials or building auxiliaries. Accordingly, the building materials or building auxiliaries may be subsequently treated or already treated building materials or building auxiliaries, for example sealing compounds, may be re-charged after prolonged use by application of the preparations according to the invention.

The building materials or building auxiliaries treated in accordance with the invention are preferably selected from adhesives, sealing compounds, surfacing compounds and coating compositions, plastics, lacquers, paints, plaster, mortar, screed, concrete, insulating materials and primers. Particularly preferred building materials or building auxiliaries are jointing compounds (for example silicone-containing jointing compounds), wallpaper pastes, plaster, carpet adhesives, silicone adhesives, dispersion paints, coating compositions for interiors and/or exteriors and tile adhesives.

Sealing compounds and, more particularly, jointing compounds typically contain organic polymers and, in many cases, mineral or organic fillers and other additives.

Suitable polymers are, for example, the thermoplastic elastomers described in applicants' DE-A-3602526, preferably polyurethanes and acrylates. Suitable polymers are also mentioned in applicants' DE-A 3726547, DE-A 4029504 and DE-A 4009095 and in DE-A1 9704553 and DE-A 4233077, of which the fill disclosures are included herein.

The sealing compounds (sealants or sealant mixtures) preferably contain 0.0001 to 1.5% by weight of eugenol and/or eugenol derivatives. Concentrations of 0.001 to 0.5% by weight are particularly preferred.

According to the invention, the sealants according to the invention may be treated both in the uncured state and after curing at <60° C. In the context of the invention, sealants are materials conforming to DIN EN 26927, more particularly those which cure plastically or elastically as sealants. The sealants according to the invention may contain any of the additives typical of the corresponding sealing compounds, such as for example typical thickeners, reinforcing fillers, crosslinking catalysts, pigments, coupling agents or other volume extenders. Sealants containing eugenol and/or eugenol derivatives may be incorporated both in the final sealing compounds and in parts thereof or together with one or more components of the sealing compounds by dispersion in known manner, for example by using dispersing machines, kneaders, planetary mixers, etc., in the absence of moisture and oxygen.

Even the treatment of already cured, crosslinked sealant surfaces can be carried out by applying solutions or suspensions of the substance used in accordance with the invention so that the active component is transported into the sealing compound by swelling or diffusion.

Sealants usable in accordance with the invention may be based on silicones, urethanes and acrylates. Urethane-based sealants are disclosed, for example, in Ullmann's Encyclopedia of Industrial Chemistry ($8^{th}$ Edition 2003, Chapter 4) and in U.S. Pat. No. 4,417,042.

Silicone sealants are known to the expert, for example from EP 0 118 030 A, EP 0 3161 591 A, EP 0 327 847 A, EP 0 553 143 A, DE 195 49 425 A and U.S. Pat. No. 4,417,042.

Examples of acrylate sealants are disclosed inter alia in WO 01/09249 and in U.S. Pat. No. 5,077,360.

Systems crosslinking at room temperature, as described for example in EP 0 327 847 and U.S. Pat. No. 5,077,360, are particularly preferred. These systems may be single- or multi-component systems (in multicomponent systems, the catalyst and crosslinking agent may be separately present, as disclosed, for example, in U.S. Pat. No. 4,891,400 and in U.S. Pat. No. 5,502,144) or other so-called silicone RVT two-component systems, more particularly platinum-free systems.

Particularly preferred systems are so-called one-component systems which contain all the ingredients for making a sealing compound, are stored in the absence of atmospheric moisture and/or oxygen and cure in situ by reacting with atmospheric oxygen. So-called silicone neutral systems, in which the reaction of crosslinking agents with the water or ambient air does not lead to corrosive, acidic, basic or odor-intensive decomposition products, are particularly preferred. Examples of such systems are disclosed in DE 195 49 425, in U.S. Pat. No. 4,417,042 and in EP 0 327 847.

The sealing compounds and, more particularly, jointing compounds may contain aqueous or organic solvents. Suitable organic solvents are hydrocarbons, such as cyclohexane, toluene or even xylene or petroleum ether. Other solvents are ketones, such as methylbutylketone, and chlorinated hydrocarbons.

The sealing compounds may also contain other rubber-like polymers, including relatively low molecular weight, commercial types of polyisobutylene, polyisoprene or even polybutadiene styrene. Degraded natural rubber or neoprene rubber may also be used. It is even possible to use types still liquid at room temperature which are commonly referred to as "liquid rubber".

The sealing compounds according to the invention may be used to join materials of various different kinds to one another or to seal them. The materials in question are, primarily, concrete, glass, plaster and/or enamels, ceramic and china. However, moldings or profiles of aluminium, steel, zinc or even plastics, such as PVC or polyurethanes or acrylic resins, may also be joined or sealed. Finally, the sealing of wood or wood materials to various other materials is also mentioned.

The stability of jointing compounds is generally attributable to the addition of fine-particle solids—also known as fillers. These fillers may be divided into organic and inorganic types. Preferred inorganic fillers are, for example, silica, silicon dioxide (coated or uncoated), chalk (coated or uncoated) and/or zeolites. The zeolites may also act as drying agents. A suitable organic filler is, for example, PVC powder. The fillers generally make a key contribution to the sealing compound having the necessary inner cohesion after application so that it does not run or bulge out from vertical joints. The additives or fillers mentioned may be divided into pigments and thixotropicizing fillers—also known in short as thixotropicizing agents.

Suitable thixotropicizing agents are any of the known types, such as bentones, kaolins or even organic compounds, such as hydrogenated castor oil or derivatives thereof with polyfunctional amines or the reaction products of stearic acid or ricinoleic acid with ethylenediamine. It has proved to be particularly favorable to use silica, more particularly pyrolysis silica. Other suitable thixotropicizing agents are substantially swellable polymer powders, for example polyacrylonitrile, polyurethane, polyvinyl chloride, polyacrylates, polyvinyl alcohols, polyvinyl acetate and the corresponding copolymers. Particularly good results are obtained with fine-particle polyvinyl chloride powder. Besides the thixotropicizing agents, coupling agents, such as mercaptoalkyl silane for example, may also be used. It has proved to be useful in this regard to use a monomercaptoalkyl trialkoxysilane. Mercaptopropyl trimethoxysilane, for example, is commercially available.

The properties of a jointing compound can be further improved by adding other components to the polymer powder used as thixotropicizing agent. Such components fall into the category of plasticizers or swelling agents and swelling auxiliaries used for plastics.

Plasticizers from the class of phthalates, for example, may be used, more particularly for urethane- or acrylate-based sealing compounds. Examples of suitable compounds from this class are dioctyl phthalate, dibutyl phthalate and benzyl butyl phthalate. Other suitable classes of compounds are chloroparaffins, alkyl sulfonic acid esters, for example phenols or cresols, and fatty acid esters.

Suitable plasticizers for silicone sealing compounds are silicone oils, more particularly polydimethyl siloxanes, and hydrocarbons and/or mixtures thereof, more particularly hydrocarbons with a boiling point above 200° C. and more particularly above 230° C.

Suitable swelling auxiliaries are low molecular weight organic substances which are miscible with the polymer powder and the plasticizer. Representatives of swelling auxiliaries such as these can be found by the expert in the relevant textbooks on plastics and polymers. Preferred swelling auxiliaries for polyvinyl chloride powders are esters, ketones, aliphatic hydrocarbons, aromatic hydrocarbons and alkyl-substituted aromatic hydrocarbons.

The pigments and dyes used may be any of those already used for the applications in question, such as titanium dioxide, iron oxides and carbon black.

In order to improve stability in storage, stabilizers, such as benzoyl chloride, acetyl chloride, toluenesulfonic acid methyl ester, carbodiimides and/or polycarbodiimides, may be added to the sealing compounds, as already known. Olefins containing 8 to 20 carbon atoms have proved to be particularly effective stabilizers. Besides their stabilizing effect, these stabilizers can also act as plasticizers or swelling agents. Preferred stabilizers are olefins containing 8 to 18 carbon atoms, particularly if the double bond is in the 1,2-position. The best results are obtained when the molecular structure of these stabilizers is linear.

By using eugenol and/or eugenol derivatives in accordance with the invention for inhibiting the asexual propagation of fungi, the problem of biocide resistance being built up is avoided. Where eugenol and/or eugenol derivatives are used in building materials and building auxiliaries susceptible to molds, more particularly in adhesives, coating compositions and sealing compounds and especially jointing compounds, several desirable effects are achieved through the inhibition of sporulation:
a) discoloration by pigmented spores is prevented,
b) the spread of the mold infestation is delayed,
c) the release of allergens is reduced.

In another preferred embodiment, the present invention relates to wallpaper adhesives containing 0.000001 to 2% by weight of eugenol and/or eugenol derivatives. Wallpaper pastes are prepared from aqueous solutions of hydrocolloids, such as methyl cellulose, methyl hydroxypropyl cellulose or water-soluble starch derivatives. Aqueous dispersions of film-forming high molecular weight, such as polyvinyl acetate, may also be used, particularly in conjunction with the cellulose and starch derivatives already mentioned.

The filter media used may be any of the known types providing they are suitable for use in water or air filter systems, for more particularly for air conditioning systems or room humidifiers or dehumidifiers. Filter materials of cellulose, glass fibers, PVC fibers, polyester fibers, polyamide fibers, more particularly nylon fibers, nonwovens, sintered materials and membrane filters are particularly mentioned.

The concentration of eugenol and/or eugenol derivatives used for inhibiting the asexual propagation of fungi in the compositions according to the invention may be varied within wide limits by the expert according to the conditions under which the preparations are used.

The laundry detergents and/or cleaning compositions according to the invention contain 0.000001 to 2% by weight of eugenol and/or eugenol derivatives. Concentrations of 0.00001 to 1.0% by weight and more especially 0.0001 to 0.1% by weight are particularly preferred. In a most particularly preferred embodiment, the laundry detergents and cleaning compositions contain 0.001 to 0.01% by weight of these compounds.

The preparations according to the invention are produced to standard formulations known to the expert. Eugenol and/or eugenol derivatives are preferably added to the ready-to-use preparations although, if desired, they may also be added during the production process.

Inhibiting the asexual propagation of fungi on textiles or plastic surfaces often prevents re-infection of already infested parts of the body. Inhibiting the asexual propagation of fungi on ceramics, plastics or metals reduces the risk of infection of re-infection without contaminating the skin, mucous membrane or wastewaters with fungicidal or fungistatic components. Catheters and other surgical instruments and/or prostheses made of plastic or metals can also be kept largely free from fungi by the use of substances which release terpenes and/or perfume alcohols, for example in rinses or cleaning preparations.

In another particular embodiment, eugenol and/or eugenol derivatives are added to laundry detergents and/or cleaners. In particular, modern textile fibers which cannot be washed with heavy-duty detergents or at high temperatures cannot be completely freed from fungi by typical light-duty detergents or washing temperatures of 30 or 40° C. One advantage of using such substances usable in accordance with the invention in laundry detergents and cleaning compositions is that articles of clothing can be kept free from fungi despite minimal wastewater pollution and a low risk of resistance buildup.

According to the invention, eugenol and/or eugenol derivatives may also be added to cleaning compositions used for cleaning hard surfaces, for example floors, tiles, plastics and other hard surfaces in the home, more particularly in humid rooms (for example bathrooms) or in medical practices. Here they are able to prevent the unwanted discoloration of surfaces through the formation of colored spores (for example black from *Aspergillus niger*). Shower curtains and other bathroom textiles can also be kept free from discoloration by spores.

In the context of the invention, laundry detergents and cleaning compositions are understood in the broadest sense to be surfactant-containing preparations in solid form (particles, powders, etc.), semisolid form (pastes, etc.), liquid form (solutions, emulsions, suspensions, gels, etc.) and gas-like form (aerosols, etc.) which, to achieve an advantageous effect in use, contain one or more surfactants, normally besides other components typical of the particular application. Examples of such surfactant-containing preparations are surfactant-containing laundry detergent preparations, surfactant-containing cleaners for hard surfaces or surfactant-containing fabric conditioning preparations which may be solid or liquid or even present in a form which comprises solid and liquid components or partial amounts of the components alongside one another.

The laundry detergents and cleaners may contain typical ingredients, such as anionic, nonionic, cationic and amphoteric surfactants, inorganic and organic builders, special polymers (for example those with co-builder properties), foam inhibitors, dyes and optionally additional perfumes, bleaching agents (for example peroxo bleaching agents and chlorine bleaching agents), bleach activators, bleach stabilizers, bleach catalysts, enzymes and redeposition inhibitors without the ingredients being confined to these groups of substances. Important other ingredients of such preparations are often washing auxiliaries including, for example, optical brighteners, UV absorbers, soil repellents, i.e. polymers which counteract the resoiling of fibers. The individual groups of substances are explained in more detail in the following.

In cases where the preparations are present at least partly in the form of shaped bodies, binders and disintegration aids may also be present.

The surfactants used may be anionic, nonionic, zwitterionic and cationic surfactants.

Suitable anionic surfactants are, for example, those of the sulfonate and sulfate type. Suitable surfactants of the sulfonate type are preferably $C_{9-13}$ alkyl benzenesulfonates, olefin sulfonates, i.e. mixtures of alkene and hydroxyalkane sulfonates, and the disulfonates obtained, for example, from $C_{12-18}$ monoolefins with an internal or terminal double bond by sulfonation with gaseous sulfur trioxide and subsequent alkaline or acidic hydrolysis of the sulfonation products. Other suitable surfactants of the sulfonate type are the alkane sulfonates obtained from $C_{12-18}$ alkanes, for example by sulfochlorination or sulfoxidation and subsequent hydrolysis or neutralization. The esters of 2-sulfofatty acids (ester sulfonates), for example the 2-sulfonated methyl esters of hydrogenated coconut oil, palm kernel oil or tallow fatty acids, are also suitable.

Other suitable anionic surfactants are sulfonated fatty acid glycerol esters. Fatty acid glycerol esters in the context of the present invention are the monoesters, diesters and triesters and mixtures thereof which are obtained where production is carried out by esterification of a monoglycerol with 1 to 3 mol fatty acid or in the transesterification of triglycerides with 0.3 to 2 mol glycerol. Preferred sulfonated fatty acid glycerol esters are the sulfonation products of saturated fatty acids containing 6 to 22 carbon atoms, for example caproic acid, caprylic acid, capric acid, myristic acid, lauric acid, palmitic acid, stearic acid or behenic acid.

Preferred alk(en)yl sulfates are the alkali metal salts and, in particular, the sodium salts of the sulfuric acid semiesters of $C_{12-18}$ fatty alcohols, for example cocofatty alcohol, tallow fatty alcohol, lauryl, myristyl, cetyl or stearyl alcohol, or $C_{10-20}$ oxoalcohols and the corresponding semiesters of secondary alcohols with the same chain length. Other preferred alk(en)yl sulfates are those with the chain length mentioned which contain a synthetic, linear alkyl chain based on a petrochemical and which are similar in their degradation behavior to the corresponding compounds based on oleochemical raw materials. $C_{12-16}$ alkyl sulfates, $C_{12-15}$ alkyl sulfates and $C_{14-15}$ alkyl sulfates are preferred for laundry detergents and cleaners. Other suitable anionic surfactants are 2,3-alkyl sulfates which may be produced, for example, in accordance with U.S. Pat. No. 3,234,258 or U.S. Pat. No. 5,075,041 and which are commercially obtainable as products of the Shell Oil Company under the name of DAN®.

The sulfuric acid monoesters of linear or branched $C_{7-21}$ alcohols ethoxylated with 1 to 6 mol ethylene oxide, such as 2-methyl-branched $C_{9-11}$ alcohols containing on average 3.5 mol ethylene oxide (EO) or $C_{12-18}$ fatty alcohols containing 1 to 4 EO, are also suitable. In view of their high foaming capacity, they are only used in relatively small quantities, for example in quantities of 1 to 5% by weight, in laundry detergents and cleaners.

Other suitable anionic surfactants are the salts of alkyl sulfosuccinic acid which are also known as sulfosuccinates or as sulfosuccinic acid esters and which represent monoesters and/or diesters of sulfosuccinic acid with alcohols, preferably fatty alcohols and, more particularly, ethoxylated fatty alcohols. Preferred sulfosuccinates contain $C_{8-18}$ fatty alcohol residues or mixtures thereof. Particularly preferred sulfosuccinates contain a fatty alcohol residue derived from ethoxylated fatty alcohols which, considered in isolation, represent nonionic surfactants (for a description, see below). Of these sulfosuccinates, those of which the fatty alcohol residues are derived from narrow-range ethoxylated fatty alcohols are particularly preferred. Alk(en)yl succinic acid preferably containing 8 to 18 carbon atoms in the alk(en)yl chain or salts thereof may also be used.

Other suitable anionic surfactants are, in particular, soaps. Suitable soaps are saturated fatty acid soaps, such as the salts of lauric acid, myristic acid, palmitic acid, stearic acid, hydrogenated erucic acid and behenic acid, and soap mixtures derived in particular from natural fatty acids, for example coconut oil, palm kernel oil or tallow fatty acids.

The anionic surfactants, including the soaps, may be present in the form of their sodium, potassium or ammonium salts and as soluble salts of organic bases, such as mono-, di- or triethanolamine. The anionic surfactants are preferably present in the form of their sodium or potassium salts and, more preferably, in the form of their sodium salts. The surfactants may also be used in the form of their magnesium salts.

According to the invention, preferred compositions contain 5 to 50% by weight, preferably 7.5 to 40% by weight and more preferably 15 to 25% by weight of one or more anionic surfactants.

Preferred nonionic surfactants are alkoxylated, advantageously ethoxylated, more especially primary alcohols preferably containing 8 to 18 carbon atoms and, on average, 1 to 12 mol ethylene oxide (EO) per mol alcohol, in which the alcohol component may be linear or, preferably, methyl-branched in the 2-position or may contain linear and methyl-branched residues in the form of the mixtures typically present in oxoalcohol residues. However, alcohol ethoxylates containing linear residues of alcohols of native origin with 12 to 18 carbon atoms, for example coconut oil, palm oil, tallow or oleyl alcohol, and on average 2 to 8 EO per mol alcohol are particularly preferred. Preferred ethoxylated alcohols include, for example, $C_{12-14}$ alcohols containing 3 EO or 4 EO, $C_{9-11}$ alcohol containing 7 EO, $C_{13-15}$ alcohols containing 3 EO, 5 EO, 7 EO or 8 EO, $C_{12-18}$ alcohols containing 3 EO, 5 EO or 7 EO and mixtures thereof, such as mixtures of $C_{12-14}$ alcohol containing 3 EO and $C_{12-18}$ alcohol containing 5 EO. The degrees of ethoxylation mentioned represent statistical mean values which, for a special product, can be a whole number or a broken number. Preferred alcohol ethoxylates have a narrow homolog distribution (narrow range ethoxylates, NRE). In addition to these nonionic surfactants, fatty alcohols containing more than 12 EO may also be used, examples including tallow fatty alcohol containing 14 EO, 25 EO, 30 EO or 40 EO.

Another class of preferred nonionic surfactants which may be used either as sole nonionic surfactant or in combination with other nonionic surfactants are alkoxylated, preferably ethoxylated or ethoxylated and propoxylated, fatty acid alkyl esters preferably containing 1 to 4 carbon atoms in the alkyl chain, more especially the fatty acid methyl esters.

Another class of nonionic surfactants which may advantageously be used are the alkyl polyglycosides (APGs). Suitable alkyl polyglycosides correspond to the general formula $RO(G)_z$ where R is a linear or branched, more particularly 2-methyl-branched, saturated or unsaturated aliphatic radical containing 8 to 22 and preferably 12 to 18 carbon atoms and G stands for a glycose unit containing 5 or 6 carbon atoms, preferably glucose. The degree of glycosidation z is between 1.0 and 4.0, preferably between 1.0 and 2.0 and more preferably between 1.1 and 1.4.

Linear alkyl polyglucosides, i.e. alkyl polyglycosides in which the polyglycosyl component is a glucose unit and the alkyl component is an n-alkyl group, are preferably used.

The surfactant-containing preparations according to the invention may advantageously contain alkyl polyglycosides, APG contents of more than 0.2% by weight, based on the preparation as a whole, being preferred for laundry detergent, dishwashing detergent or cleaning preparations. Particularly preferred surfactant-containing preparations contain APGs in quantities of 0.2 to 10% by weight, preferably in quantities of 0.2 to 5% by weight and more preferably in quantities of 0.5 to 3% by weight.

Nonionic surfactants of the amine oxide type, for example N-cocoalkyl-N,N-dimethylamine oxide and N-tallowalkyl-N,N-dihydroxyethylamine oxide, and the fatty acid alkanolamide type are also suitable. The quantity in which these nonionic surfactants are used is preferably no more than the quantity in which the ethoxylated fatty alcohols are used and, more preferably, no more than half that quantity.

Other suitable surfactants are polyhydroxyfatty acid amides corresponding to formula (I):

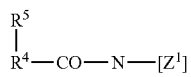

(I)

in which $R^4CO$ is an aliphatic acyl group containing 6 to 22 carbon atoms, $R^5$ is hydrogen, an alkyl or hydroxyalkyl group containing 1 to 4 carbon atoms and $[Z^1]$ is a linear or branched polyhydroxyalkyl group containing 3 to 10 carbon atoms and 3 to 10 hydroxyl groups. The polyhydroxyfatty acid amides are known substances which may normally be obtained by reductive amination of a reducing sugar with ammonia, an alkylamine or an alkanolamine and subsequent acylation with a fatty acid, a fatty acid alkyl ester or a fatty acid chloride.

The group of polyhydroxyfatty acid amides also includes compounds corresponding to formula (II):

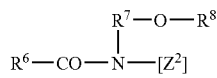

(II)

in which $R^6$ is a linear or branched alkyl or alkenyl group containing 7 to 12 carbon atoms, $R^7$ is a linear, branched or cyclic alkyl group or an aryl group containing 2 to 8 carbon atoms and $R^8$ is a linear, branched or cyclic alkyl group or an aryl group or an oxyalkyl group containing 1 to 8 carbon atoms, $C_{1-4}$ alkyl or phenyl groups being preferred, and $[Z^2]$ is a linear polyhydroxyalkyl group, of which the alkyl chain is substituted by at least two hydroxyl groups, or alkoxylated, preferably ethoxylated or propoxylated, derivatives of that group.

$[Z^2]$ is preferably obtained by reductive anination of a reduced sugar, for example glucose, fructose, maltose, lactose, galactose, mannose or xylose. The N-alkoxy- or N-aryloxy-substituted compounds may then be converted into the required polyhydroxyfatty acid amides by reaction with fatty acid methyl esters in the presence of an alkoxide as catalyst, for example in accordance with the teaching of International patent application WO-A-95/07331.

In another preferred embodiment, cationic surfactants may be used in addition to anionic and nonionic surfactants.

Fabric-softening substances include, in particular, cationic surfactants. Examples of cationic surfactants are, in particular, quaternary ammonium compounds, cationic polymers and emulsifiers.

Suitable examples are quaternary ammonium compounds corresponding to formulae (III) and (IV):

(III)

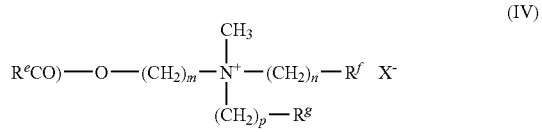

(IV)

where $R^a$ and $R^b$ in (IV) represent an acyclic alkyl group containing 12 to 24 carbon atoms, $R^c$ is a saturated $C_{1-4}$ alkyl or hydroxyalkyl group, $R^d$ is either the same as $R^a$, $R^b$ or $R^c$ or represents an aromatic radical. $X^-$ is either a halide, methosulfate, methophosphate or phosphate ion or a mixture thereof. Examples of cationic compounds corresponding to formula (III) are didecyl dimethyl ammonium chloride, ditallow dimethyl ammonium chloride or dihexadecyl ammonium chloride.

Compounds corresponding to formula (IV) are so-called esterquats. Esterquats are distinguished by excellent biodegradability. In that formula, $R^e$ is an aliphatic alkyl group containing 12 to 22 carbon atoms and 0, 1, 2 or 3 double bonds, $R^f$ is H, OH or $O(CO)R^h$, $R^g$ independently of $R^f$ stands for H. OH or $O(CO)R^i$, $R^h$ and $R^i$ independently of one another representing an aliphatic acyl group containing 12 to 22 carbon atoms and 0, 1, 2 or 3 double bonds. m, n and p independently of one another can have a value of 1, 2 or 3. $X^-$ can be a halide, methosulfate, methophosphate or phosphate ion or a mixture thereof. Preferred compounds contain the group $O(CO)R^h$ for $R^f$ and $C_{16-18}$ alkyl groups for $R^e$ and $R^h$. Particularly preferred compounds are those in which $R^g$ is also OH. Examples of compounds corresponding to formula (IV) are methyl-N-(2-hydroxyethyl)-N,N-di(tallowacyloxyethyl)-ammonium metho-sulfate, bis-(palmitoyl)-ethyl hydroxyethyl methyl ammonium methosulfate or methyl-N, N-bis-(acyloxyethyl)-N-(2-hydroxyethyl)-ammonium methosulfate. If quaternized compounds corresponding to formula (IV) containing unsaturated alkyl chains are used, the acyl groups of which the corresponding fatty acids have an iodine value of 5 to 80, preferably 10 to 60 and more particularly 15 to 45 and which have a cis-:trans-isomer ratio (in % by weight) of greater than 30:70, preferably greater than 50:50 and more particularly greater than 70:30 are preferred. Commercially available examples are the methyl hydroxyalkyl dialkoyloxyalkyl ammonium methosulfates marketed by Stepan under the name of Stepantex® or the Cogris products known under the name of Dehyquart® or the Goldschmidt-Witco products known under the name of Rewoquat®. Other preferred compounds are the diesterquats corresponding to formula (III) which are obtainable under the name of Rewoquat® W 222 LM or CR 3099 and, besides softness, also provide for stability and color protection.

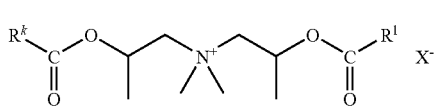

In formula (V), $R^k$ and $R^l$ independently of one another each represent an aliphatic acyl group containing 12 to 22 carbon atoms and 0, 1, 2 or 3 double bonds.

Besides the quaternary compounds described above, other known compounds may also be used, including for example quaternary imidazolinium compounds corresponding to formula (VI):

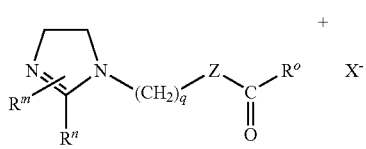

in which $R^m$ represents H or a saturated alkyl group containing 1 to 4 carbon atoms, $R^n$ and $R^o$ independently of one another represent an aliphatic, saturated or unsaturated alkyl group containing 12 to 18 carbon atoms, $R^n$ alternatively may also represent $O(CO)R^p$, $R^p$ being an aliphatic, saturated or unsaturated alkyl group containing 12 to 18 carbon atoms, and Z is an NH group or oxygen and $X^-$ is an anion. q may be an integer of 1 to 4.

Other suitable quaternary compounds correspond to formula (VII):

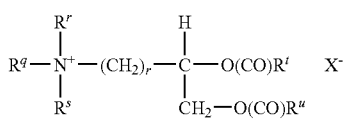

where $R^q$, $R^r$ and $R^s$ independently of one another represent a $C_{1-4}$ alkyl, alkenyl or hydroxyalkyl group, $R^t$ and $R^u$ independently of one another represent a $C_{8-28}$ alkyl group and r is a number of 0 to 5.

Besides the compounds corresponding to formulae (III) and (VII), short-chain, water-soluble quaternary ammonium compounds may also be used, including trihydroxyethyl methyl ammonium methosulfate or the alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride.

Protonated alkylamine compounds with a fabric-softening effect and non-quaternized protonated precursors of the cationic emulsifiers are also suitable.

Other cationic compounds suitable for use in accordance with the invention are the quaternized protein hydrolyzates.

Suitable cationic polymers are the polyquaternium polymers listed in the CTFA Cosmetic Ingredient Dictionary (The Cosmetic, Toiletry and Fragrance Association, Inc., 1997), more particularly the polyquaternium-6, polyquatemium-7 and polyquatemium-10 polymers (Ucare Polymer IR 400, Amerchol) also known as merquats, polyquatemium-4 copolymers, such as graft copolymers with a cellulose skeleton and quaternary ammonium groups attached by allyl dimethyl ammonium chloride, cationic cellulose derivatives, such as cationic guar, such as guar hydroxypropyl triammonium chloride, and similar quaternized guar derivatives (for example Cosmedia Guar, Cognis GmbH), cationic quaternary sugar derivatives (cationic alkyl polyglucosides), for example the commercial product Glucquat®100 (CTFA name: Lauryl Methyl Gluceth-10 Hydroxypropyl Dimonium Chloride), copolymers of PVP and dimethyl aminomethacrylate, copolymers of vinyl imidazole and vinyl pyrrolidone, aminosilicon polymers and copolymers.

Polyquaternized polymers (for example Luviquat Care, BASF) and chitin-based cationic biopolymers and derivatives thereof, for example the polymer commercially obtainable as Chitosan® (Cognis), are also suitable.

Cationic silicone oils are also suitable for the purposes of the invention, including for example the commercially available products Q2-7224 (a stabilized trimethylsilyl amodimethicone, Dow Corning), Dow Corning 929 Emulsion (containing a hydroxylamino-modified silicone which is also known as amodimethicone), SM-2059 (General Electric), SLM-55067 (Wacker), Abil®-Quat 3270 and 3272 (diquaternary polydimethylsiloxanes, quatemium-80, Goldschmidt-Rewo) and siliconequat Rewoquat® SQ 1 (Tegopren® 6922, Goldschmidt-Rewo).

Other suitable compounds correspond to formula (VIII):

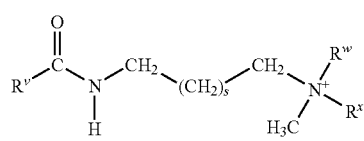

and may be alkylamidoamines in their non-quaternized form or, as illustrated, their quaternized form. In formula (VIII), $R^v$ may be an aliphatic acyl group containing 12 to 22 carbon atoms and 0, 1, 2 or 3 double bonds. s may assume a value of 0 to 5. $R^w$ and $R^x$ independently of one another represent H, $C_{1-4}$ alkyl or hydroxyalkyl. Preferred compounds are fatty acid amidoamines, such as the stearylamidopropyl dimethylamine obtainable under the name of Tego Amid® S 18 or the 3-tallowamidopropyl trimethylammonium methosulfate obtainable as Stepantex® X 9124, which, besides a good conditioning effect, are also distinguished by a dye transfer inhibiting effect and by ready biodegradability.

If cationic surfactants are used, they are preferably present in the preparations in quantities of 0.01 to 10% by weight and more particularly in quantities of 0.1 to 3.0% by weight.

The total surfactant content of the compositions according to the invention may be between 5 and 50% by weight and is preferably between 10 and 35% by weight.

Next to surfactants, builders are the most important ingredients of detergents and cleaning compositions. The surfactant-containing preparations according to the invention may contain any of the builders typically used in detergents, i.e. in particular zeolites, silicates, carbonates, organic co-builders and—providing there are no ecological objections to their use—the phosphates.

Suitable crystalline layer-form sodium silicates correspond to the general formula $NaMSi_xO_{2x+1}.H_2O$, where M is sodium or hydrogen, x is a number of 1.9 to 4 and y is a number of 0 to 20, preferred values for x being 2, 3 or 4. Crystalline layer silicates such as these are described, for example, in European patent application EP-A-0 164 514. Preferred crystalline layer silicates corresponding to the above formula are those in which M is sodium and x assumes the value 2 or 3. Both - and -sodium disilicates $Na_2Si_2O_5.y$ $H_2O$ are particularly preferred, -sodium disilicate being obtainable, for example, by the process described in International patent application WO-A-91/08171.

Other useful builders are amorphous sodium silicates with a modulus ($Na_2O:SiO_2$ ratio) of 1:2 to 1:3.3, preferably 1:2 to 1:2.8 and more preferably 1:2 to 1:2.6 which dissolve with delay and exhibit multiple wash cycle properties. The delay in dissolution in relation to conventional amorphous sodium silicates can have been obtained in various ways, for example by surface treatment, compounding, compacting or by over-drying. So-called X-ray amorphous silicates, which also dissolve with delay in relation to conventional waterglasses, are described for example in German patent application DE-A-44 00 024. The products have microcrystalline regions between 10 and a few hundred nm in size, values up to at most 50 nm and more particularly up to at most 20 nm being preferred. Compacted amorphous silicates, compounded amorphous silicates and overdried X-ray-amorphous silicates are particularly preferred.

A finely crystalline, synthetic zeolite containing bound water optionally used is preferably zeolite A and/or zeolite P. Zeolite MAP® (for example Doucil A24 obtainable from Crosfield) is a particularly preferred P-type zeolite. However, zeolite X and mixtures of A, X and/or P are also suitable. According to the invention, it is also preferred to use, for example, a co-crystallizate of zeolite X and zeolite A (ca. 80% by weight zeolite X) which is marketed by CONDEA Augusta S.p.A. under the name of VEGOBOND AX® and which may be described by the following formula:

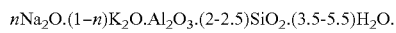

$nNa_2O.(1-n)K_2O.Al_2O_3.(2-2.5)SiO_2.(3.5-5.5)H_2O$.

Suitable zeolites have a mean particle size of less than 10 m (volume distribution, as measured by the Coulter Counter Method) and contain preferably 18 to 22% by weight and more preferably 20 to 22% by weight of bound water.

The generally known phosphates may of course also be used as builders in detergents providing their use should not be avoided on ecological grounds. The sodium salts of the orthophosphates, the pyrophosphates and above all the tripolyphosphates are particularly suitable.

Suitable organic builders are, for example, polycarboxylic acids usable in the form of their sodium salts, polycarboxylic acids being understood to be carboxylic acids which carry more than one acid function, for example citric acid, adipic acid, succinic acid, glutaric acid, malic acid, tartaric acid, maleic acid, fumaric acid, sugar acids, aminocarboxylic acids, nitrilotriacetic acid (NTA), providing its use is not ecologically unsafe, and mixtures thereof. Preferred salts are the salts of the polycarboxylic acids, such as citric acid, adipic acid, succinic acid, glutaric acid, tartaric acid, sugar acids and mixtures thereof. The acids per se may also be used. Besides their builder effect, the acids also typically have the property of an acidifying component and, hence, also serve to establish a relatively low and mild pH value in surfactant-containing preparations. Citric acid, succinic acid, glutaric acid, adipic acid, gluconic acid and mixtures thereof are particularly mentioned in this regard.

Other suitable builders are polymeric polycarboxylates, for example alkali metal salts of polyacrylic acid or polymethacrylic acid, for example those with a relative molecular weight of 500 to 70,000 g/mol.

The molecular weights mentioned in this specification for polymeric polycarboxylates are weight-average molecular weights $M_w$ of the particular acid form which, basically, were determined by gel permeation chromatography (GPC) using a UV detector. The measurement was made against an external polyacrylic acid standard which provides realistic molecular weight values by virtue of its structural relationship to the polymers investigated. These values differ significantly from the molecular weight values where polystyrene sulfonic acids are used as the standard. The molecular weights measured against polystyrene sulfonic acids are generally higher than the molecular weights mentioned in the present specification.

Suitable polymers are, in particular, polyacrylates which preferably have a molecular weight of 12,000 to 30,000 g/mol. Within this group, the short-chain polyacrylates which have molecular weights of 2,000 to 10,000 g/mol and more especially 3,000 to 5,000 g/mol are preferred by virtue of their superior solubility.

Other suitable polymers are copolymeric polycarboxylates, more particularly those of acrylic acid with methacrylic acid or of acrylic acid or methacrylic acid with maleic acid. Copolymers of acrylic acid with maleic acid which contain 50 to 90% by weight acrylic acid and 50 to 10% by weight maleic acid have proved to be particularly suitable. Their relative molecular weight, based on free acids, is generally in the range from 2,000 to 70,000 g/mol, preferably in the range from 20,000 to 50,000 g/mol and more particularly in the range from 30,000 to 40,000 g/mol.

The (co)polymeric polycarboxylates may be used either as powders or in the form of an aqueous solution. The content of (co)polymeric polycarboxylates in the detergents/cleaners according to the invention is preferably between 0.5 and 20% by weight and more particularly between 3 and 10% by weight.

In order to improve solubility in water, the polymers may also contain allyl sulfonic acids, such as allyloxy benzenesulfonic acid and methallyl sulfonic acid, as monomer.

Other particularly preferred polymers are biodegradable polymers of more than two different monomer units, for example those which contain salts of acrylic acid and maleic acid and vinyl alcohol or vinyl alcohol derivatives as monomers or those which contain salts of acrylic acid and 2-alkylallyl sulfonic acid and sugar derivatives as monomers.

Other preferred copolymers are those which preferably contain acrolein and acrylic acid/acrylic acid salts or acrolein and vinyl acetate as monomers.

Other preferred builders are polymeric aminodicarboxilic acids, salts or precursors thereof. Polyaspartic acids or salts and derivatives thereof, which have a bleach-stabilizing effect in addition to their co-builder properties, are particularly preferred.

Other suitable builders are polyacetals which may be obtained by reaction of dialdehydes with polyol carboxylic acids containing 5 to 7 carbon atoms and at least three hydroxy groups. Preferred polyacetals are obtained from dialdehydes, such as glyoxal, glutaraldehyde, terephthalaldehyde and mixtures thereof and from polyol carboxylic acids, such as gluconic acid and/or glucoheptonic acid.

Other suitable organic builders are dextrins, for example oligomers or polymers of carbohydrates which may be obtained by partial hydrolysis of starches. The hydrolysis may be carried out by standard methods, for example acid- or enzyme-catalyzed methods. The end products are preferably hydrolysis products with average molecular weights of 400 to 500,000 g/mol. A polysaccharide with a dextrose equivalent (DE) of 0.5 to 40 and, more particularly, 2 to 30 is preferred, the DE being an accepted measure of the reducing effect of a polysaccharide by comparison with dextrose which has a DE of 100. Both maltodextrins with a DE of 3 to 20 and dry glucose sirups with a DE of 20 to 37 and also so-called yellow dextrins and white dextrins with relatively high molecular weights of 2,000 to 30,000 may be used. A preferred dextrin is described in British patent application 94 19 091.

The oxidized derivatives of such dextrins are their reaction products with oxidizing agents which are capable of oxidizing at least one alcohol function of the saccharide ring to the carboxylic acid function. An oxidized oligosaccharide is also suitable; a product oxidized at $C_6$ of the saccharide ring can be particularly advantageous.

Other suitable co-builders are oxydisuccinates and other derivatives of disuccinates, preferably ethylenediamine disuccinate. Ethylenediamine-N,N'-disuccinate (EDDS) is preferably used in the form of its sodium or magnesium salts. Glycerol disuccinates and glycerol trisuccinates are also particularly preferred in this connection. The quantities used in zeolite-containing and/or silicate-containing formulations are from 3 to 15% by weight.

Other useful organic co-builders are, for example, acetylated hydroxycarboxylic acids and salts thereof which may optionally be present in lactone form and which contain at least 4 carbon atoms, at least one hydroxy group and at most two acid groups.

Another class of substances with co-builder properties are the phosphonates, more particularly hydroxyalkane and aminoalkane phosphonates. Among the hydroxyalkane phosphonates, 1-hydroxyethane-1,1-diphosphonate (HEDP) is particularly important as a co-builder. It is preferably used in the form of a sodium salt, the disodium salt showing a neutral reaction and the tetrasodium salt an alkaline ration (pH 9). Preferred aminoalkane phosphonates are ethylenediamine tetramethylene phosphonate (EDTMP), diethylenetriamine pentamethylene phosphonate (DTPMP) and higher homologs thereof. They are preferably used in the form of the neutrally reacting sodium salts, for example as the hexasodium salt of EDTMP and as the hepta- and octasodium salt of DTPMP. Within the class of phosphonates, HEDP is preferably used as builder. The aminoalkane phosphonates also show a pronounced heavy metal binding capacity. Accordingly, it can be of advantage, particularly where the surfactant-containing preparations according to the invention also contain bleaching agents, to use aminoalkane phosphonates, more especially DTPMP, or mixtures of the phosphonates mentioned.

In addition, any compounds capable of forming complexes with alkaline earth metal ions may be used as co-builders.

Among the compounds yielding $H_2O_2$ in water which serve as bleaching agents, sodium perborate tetrahydrate and sodium perborate monohydrate are particularly important. Other useful bleaching agents are, for example, sodium percarbonate, peroxypyrophosphates, citrate perhydrates and $H_2O_2$-yielding peracidic salts or peracids, such as perbenzoates, peroxophthalates, diperazelaic acid, phthaloiminoperacid or diperdodecane dioic acid. If detergent or bleaching preparations for dishwashing machines are being produced, bleaching agents from the group of organic bleaches may also be used. Typical organic bleaching agents are diacyl peroxides, such as dibenzoyl peroxide for example. Other typical organic bleaching agents are the peroxy acids, of which alkyl peroxy acids and aryl peroxy acids are particularly mentioned as examples. Preferred representatives are (a) peroxybenzoic acid and ring-substituted derivatives thereof, such as alkyl peroxybenzoic acids, but also peroxy-α-naphthoic acid and magnesium monoperphthalate, (b) aliphatic or substituted aliphatic peroxy acids, such as peroxylauric acid, peroxystearic acid, ε-phthalimidoperoxycaproic acid [phthaloiminoperoxyhexanoic acid (PAP)], o-carboxybenzamidoperoxycaproic acid, N-nonenylamidoperadipic acid and N-nonenylamidopersuccinates and (c) aliphatic and araliphatic peroxydicarboxylic acids, such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyl-di(6-aminopercaproic acid).

In order to obtain an improved bleaching effect where washing is carried out at temperatures of 60° C. or lower, bleach activators may be incorporated in the surfactant-containing preparations. The bleach activators may be compounds which form aliphatic peroxocarboxylic acids containing preferably 1 to 10 carbon atoms and more preferably 2 to 4 carbon atoms and/or optionally substituted perbenzoic acid under perhydrolysis conditions. Substances bearing O- and/or N-acyl groups with the number of carbon atoms mentioned and/or optionally substituted benzoyl groups are suitable. Preferred bleach activators are polyacylated alkylenediamines, more particularly tetraacetyl ethylenediamine (TAED), acylated triazine derivatives, more particularly 1,5-diacetyl-2,4-dioxohexahydro-1,3,5-triazine (DADHT), acylated glycolurils, more particularly tetraacetyl glycoluril (TAGU), N-acylimides, more particularly N-nonanoyl succinimide (NOSI), acylated phenol sulfonates, more particularly n-nonanoyl or isononanoyloxybenzenesulfonate (n- or iso-NOBS), carboxylic anhydrides, more particularly phthalic anhydride, acylated polyhydric alcohols, more particularly triacetin, ethylene glycol diacetate and 2,5-diacetoxy-2,5-dihydrofuran.

In addition to or instead of the conventional bleach activators mentioned above, so-called bleach catalysts may also be incorporated in the surfactant-containing preparations. Bleach catalysts are bleach-boosting transition metal salts or transition metal complexes such as, for example, manganese-, iron-, cobalt-, ruthenium- or molybdenum-salen complexes or carbonyl complexes. Manganese, iron, cobalt, ruthenium, molybdenum, titanium, vanadium and copper complexes with nitrogen-containing tripod ligands and cobalt-, iron-, copper- and ruthenium-ammine complexes may also be used as bleach catalysts.

Suitable enzymes are those from the class of proteases, lipases, amylases, cellulases or mixtures thereof. Enzymes obtained from bacterial strains or fungi, such as *Bacillus subtilis, Bacillus licheniformis* and *Streptomyces griseus*, are particularly suitable. Proteases of the subtilisin type are preferred, proteases obtained from *Bacillus lentus* being particularly preferred. Enzyme mixtures, for example of protease and amylase or protease and lipase or protease and cellulase or of cellulase and lipase or of protease, amylase and lipase or of protease, lipase and cellulase, but especially cellulase-containing mixtures, are of particular interest. Peroxidases or oxidases have also proved to be suitable in some cases. The enzymes may be adsorbed to supports and/or encapsulated in membrane materials to protect them against premature decomposition. The percentage content of the enzymes, enzyme mixtures or enzyme granules in the surfactant-containing preparations according to the invention may be, for example, from about 0.1 to 5% by weight and is preferably from 0.1 to about 2% by weight.

A preferred group of suitable additives are optical brighteners. The optical brighteners typically used in laundry detergents may be used. Examples of optical brighteners are derivatives of diamino-stilbenedisulfonic acid or alkali metal salts thereof. Suitable optical brighteners are, for example, salts of 4,4'-bis-(2-anilino-4-morpholino-1,3,5-triazinyl-6-amino)-stilbene-2,2'-disulfonic acid or compounds of similar composition which contain a diethan-olamino group, a methylamino group, an anilino group or a 2-methoxyethylamino group instead of the morpholino group. In addition, brighteners of the substituted diphenyl styryl type, for example alkali metal salts of 4,4'-bis-(2-sulfostyryl)-diphenyl, 4,4'-bis-(4-chloro-3-sulfostyryl)-diphenyl or 4-(4-chlorostyryl)-4'-(2-sulfostyryl)-diphenyl, may also be present in the part-portions (detersive preparations) of the surfactant-containing preparations according to the invention. Mixtures of the brighteners mentioned above may also be used.

Another group of additives preferred for the purposes of the invention are UV absorbers. UV absorbers can be absorbed onto the treated textiles and improve the light stability of the fibers and/or the light stability of the other formulation ingredients. UV absorbers are organic substances (light filters) which are capable of absorbing ultraviolet rays and of releasing the energy absorbed in the form of longer-wave radiation, for example heat. Compounds which possess these desired properties are, for example, the compounds which act by radiationless deactivation and derivatives of benzophenone with substituents in the 2- and/or 4-position. Other suitable UV absorbers are substituted benzotriazoles such as, for example, the water-soluble benzenesulfonic acid-3-(2H-benzotriazol-2-yl)-4-hydroxy-5-(methylpropyl)-mono-sodium salt (Cibafast® H), 3-phenyl-substituted acrylates (cinnamic acid derivatives), optionally with cyano groups in the 2-position, salicylates, organic Ni complexes and natural substances, such as umbelliferone and the body's own urocanic acid. Particular significance attaches to the biphenyl and, above all, stilbene derivatives described, for example, in EP 0728749 A which are commercially available as Tinosorb® FD and Tinosorb® FR ex Ciba. Suitable UV-B absorbers include 3-benzylidene camphor or 3-benzylidene norcamphor and derivatives thereof, for example 3-(4-methylbenzylidene)-camphor as described in EP-B1 0693471; 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester; esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene); esters of salicylic acid, preferably salicylic acid-2-ethylhexyl ester, salicylic acid-4-isopropylbenzyl ester, salicylic acid homomenthyl ester; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably 4-methoxybenzmalonic acid di-2-ethylhexyl ester; triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB); propane-1,3-diones such as, for example, 1-(4-tert.butylphenyl)-3-(4'-methoxyphenyl)-propane-1,3-dione; ketotricyclo(5.2.1.0)decane derivatives as described in EP 0694521 B1. Other suitable UV-B absorbers are 2-phenylbenzimidazole-5-sulfonic acid and alkali metal, alkaline earth metal, ammonium, alkylammonium, alkanolammonium and glucammonium salts thereof; sulfonic acid derivatives of benzophenones, preferably 2-hydroxy-4-methoxybenzophenone-5-sulfonic acid and salts thereof; sulfonic acid derivatives of 3-benzylidene camphor such as, for example, 4-(2-oxo-3-bomylidenemethyl)-benzene sulfonic acid and 2-methyl-5-(2-oxo-3-bomylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789), 1-phenyl-3-(4'-isopropylphenyl)-propane-1,3-dione and the enamine compounds described in DE 19712033 A1 (BASF). The UV-A and UV-B filters may of course also be used in the form of mixtures. Besides the soluble substances mentioned, insoluble light-blocking pigments, i.e. finely dispersed, preferably "nanoized" metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. Micronized zinc oxide is preferably used. Other suitable UV filters can be found in P. Finkel's review in SÖFW-Journal 122, 543 (1996).

The UV absorbers are normally used in quantities of 0.01% by weight to 5% by weight and preferably in quantities of 0.03% by weight to 1% by weight.

Another group of additives preferably used for the purposes of the invention are dyes, particularly water-soluble or water-dispersible dyes. Preferred dyes are those of the type that are typically used in laundry and dishwasher detergents, cleaners and fabric conditioners to improve their appearance. Dyes such as these, which are not difficult for the expert to choose, have high stability in storage, are not affected by the other ingredients of the surfactant-containing preparations or by light and do not have any pronounced substantivity for textile fibers so as not to color them. According to the invention, the dyes are present in the detergents and/or cleaners according to the invention in quantities of less than 0.01% by weight.

Another class of additives which may be incorporated in accordance with the invention in the detergents and/or cleaners are polymers. Suitable polymers are, on the one hand, polymers which show co-builder properties during washing or dishwashing, i.e. for example polyacrylic acids, even modified polyacrylic acids or corresponding copolymers. Another group of polymers are polyvinyl pyrrolidone and other redeposition inhibitors, such as copolymers of polyvinyl pyrrolidone, cellulose ethers and the like. Other preferred polymers are soil repellents which are described in detail in the following.

The detergents/cleaners may also contain soil repellents as further additives according to the invention. Soil repellents are polymers which are absorbed onto the fibers and have a positive effect on the removal of oil and fats from textiles by washing, thereby counteracting resoiling. This effect becomes particularly clear when a textile which has already been repeatedly washed with a detergent according to the invention containing this oil- and fat-dissolving component is soiled. Preferred oil- and fat-dissolving components include, for example, nonionic cellulose ethers, such as methyl cellulose and methyl hydroxypropyl cellulose containing 15 to 30% by weight of methoxy groups and 1 to 15% by weight of hydroxypropoxy groups, based on the nonionic cellulose ether, and the polymers of phthalic acid and/or terephthalic acid known from the prior art or derivatives thereof, more particularly polymers of ethylene terephthalates and/or polyethylene glycol terephthalates or anionically and/or nonionically modified derivatives thereof. Of these, the sulfonated derivatives of phthalic acid and terephthalic acid polymers are particularly preferred.

Particularly where they are liquids or gels, the preparations may also contain solvents. Examples of suitable solvents are monohydric or polyhydric alcohols containing 1 to 4 carbon atoms. Preferred alcohols are ethanol, propane-1,2-diol, glycerol and mixtures thereof. The solvents may be present in liquid preparations in a quantity of 2 to 12% by weight and more particularly between about 1 and 5% by weight, based on the final preparation.

The additives mentioned are added to the detergents and/or cleaners in quantities of up to at most 30% by weight and preferably in quantities of 2 to 20% by weight.

In one particular embodiment, liquid or solid laundry detergents are particularly preferred. Light-duty laundry detergents suitable for the careful treatment of delicate textiles are also particularly preferred.

This list of detergent ingredients that may be present in the laundry/dishwashing detergents or cleaning compositions according to the invention is by no means complete and is merely intended to indicate the key ingredients typical of such compositions. In particular, organic solvents may also be present in the compositions where they are liquids or gels. These organic solvents may be mono- or polyhydric alcohols containing 1 to 4 carbon atoms. Preferred alcohols are ethanol, propane-1,2-diol, glycerol and mixtures of these alcohols. In preferred embodiments, the compositions contain 2 to 12% by weight of these alcohols. An overall particularly favorable result for hard surface cleaners is obtained when the ratio by weight of surfactant to alcohol in the solution is between about 1:1.5 and about 2:1.

Hard surface cleaners which can be applied to the surfaces in foaming or non-foaming form are also particularly preferred. The spread of mold spores in room air and the spread of discoloration attributable to mold spores in humid rooms may advantageously be reduced or prevented in this way.

Besides the constituents mentioned, the aqueous liquids used in accordance with the invention may contain other active components and additives typical of hard surface cleaners in small quantities. Examples of such active components are lime-dissolving organic acids, such as citric acid, acetic acid or lactic acid or water-soluble salts thereof, which are preferably present in quantities of 2 to 6% by weight, based on the aqueous liquid as a whole.

It can be of advantage to use a cleaner which is applied to the surface to be cleaned as a foam and thus stays longer on the surface. The cleaning effect can thus be distinctly enhanced. The foam is preferably produced immediately the liquid leaves the spray applicator. In the case of hand spray pumps, this is achieved through a special design of the spray head which ensures that the aqueous liquid issuing from the spray nozzle is mixed so intensively with air that the liquid actually impinges on the surfaces as a foam. Correspondingly designed spray pumps are commercially available. Where the cleaner is applied as an aerosol, it is important to ensure—by suitably designing the spray mechanism with the composition of the cleaning liquid in mind—that sufficient quantities of propellant gas always issue with the liquid and then cause the liquid to foam. Shaking may be necessary before application. The corresponding design of the aerosol container, intake nozzle and valve is routine to the expert and, hence, need not be further explained here. The volume of liquid sprayed onto the surface to be cleaned during the cleaning process is generally between about 10 g and about 60 g/m$^2$ and, more particularly, between 20 g and 40 g/m$^2$. The foam is preferably uniformly distributed over the surface to be cleaned and may then automatically develop its cleaning effect. Preferably, however, the surfaces are subsequently wiped with a damp cloth or a sponge, the cloth or sponge being periodically rinsed in clean water for surfaces of relatively large area. The treated surfaces may of course also be rinsed with water although this is generally unnecessary because the residues of cleaner remaining dry completely transparently and remain virtually invisible.

The following Examples are intended to illustrate the invention without limiting it in any way.

EXAMPLES

Example 1

Effect of Eugenol and Eugenol Silicic Acid Esters on the Sporulation of *Aspergillus niger*

Contamination of the surface of wort agar plates with 100 μl of a germ suspension (10$^3$ CFU/ml) of *Aspergillus niger* (DSM 1988). Various quantities of active component (solutions in ethanol, final concentrations in % by weight, see Table) were added to the agar plates beforehand. The plates were incubated for 3 days at 25° C. Sporulation was visually evaluated and the sporulation rate in [%] was determined. None of the active component concentrations used inhibited the growth of the test strain. Sporulation was inhibited with increasing concentrations and was completely suppressed at 220 μM.

TABLE 1

| | Concentration of eugenol [μm] | | | | | | | |
|---|---|---|---|---|---|---|---|---|
| | 0 | 4 | 40 | 65 | 90 | 110 | 220 | 330 | 650 |
| Sporulation [%] | 100 | 100 | 100 | 100 | 80 | 70 | 0 | 0 | 0 |

Active component: eugenol (4-allyl-2-methoxyphenol)

TABLE 2

| | Eugenol/silicic acid esters | | | |
|---|---|---|---|---|
| | Concentration of eugenol/silicic acid ester [% by wt.] | | | |
| | 0 | 0.005 | 0.01 | 0.05 |
| Sporulation [%] | 100 | 85 | 60 | 0 |

Sporulation was inhibited with increasing concentrations and was completely suppressed at a concentration of 0.05%.

Comparison Test:

Effect of Farnesol on the Sporulation of *Aspergillus niger*

TABLE 3

| | Concentration of farnesol [µm] | | | | |
|---|---|---|---|---|---|
| | 0 | 25 | 62.5 | 125 | 250 | 500 |
| Sporulation [%] | 100 | 90 | 75 | 50 | 10 | 0 |

Example 2

Effect on Eugenol on the Sporulation of *Aspergillis niger* on the Surface of an Acetate Jointing Compound Commercially available, but preservative-free, one-component silicone jointing compounds curing at room temperature (acetate system, cured 2.2×2.2×0.3 cm pieces of film) were disinfected with 70% EtOH (ethanol) and placed for 24 h in active component solutions with various concentrations (in ethanol, see Table for final concentrations). The test specimens were then re-washed twice with EtOH, rinsed with water (sterile) and dried for 24 h. The test specimens were weighed before and after this treatment and the quantity of active component in the test specimens was thus determined together with the concentration of the active component solution. The test specimens were then placed on wort agar plates and thinly coated with agar in which fungal spores had been incorporated (105 CFU/ml *Aspergillus niger*, DSM 1988). The plates were incubated for 3 days at 25° C. Sporulation was visually evaluated from the test specimens and the sporulation rate in [%] was determined. None of the active-component concentrations tested inhibited the growth of the test strain. Sporulation was inhibited by increasing concentrations of eugenol and was completely suppressed at 1.7 µm/g jointing compound. In a parallel test series with farnesol as active component, sporulation of the test strain was again inhibited, but to a far lesser extent compared with identical concentrations of eugenol.

TABLE 3

| | Concentration of eugenol [µm/g jointing compound] | | | |
|---|---|---|---|---|
| | 0 | <1 | 1.7 | ca. 3 |
| Sporulation [%] | 100 | 100 | 0 | 0 |

| | Concentration of farnesol [µm/g jointing compound] | | | |
|---|---|---|---|---|
| | 0 | 0.4 | 1.1 | 17 |
| Sporulation [%] | 100 | 100 | 100 | 30 |

Example 3

Effect of Eugenol on the Sporulation of *Aspergillus niger* on a Filter Surface After 2 Applications Filter papers (2×2 cm) were disinfected and treated twice with a 1 hour interval with 50 µl of active-component solutions differing in concentration. The test specimens were then dried. The test specimens were then placed on wort agar plates and the surface of the wort agar plates was contaminated with 100 µl of a germ suspension ($10^3$ CFU/ml) of *Aspergillus niger* (DSM 1988). The plates were incubated for 3 days at 25° C. Sporulation was visually evaluated and the sporulation rate in [%] was determined. None of the active-component concentrations tested inhibited the growth of the test strain. Sporulation was inhibited by increasing concentrations of eugenol and was 90% suppressed at 90 µm.

In a second, parallel test series with farnesol as the active component, sporulation of the test strain was again inhibited, but to a lesser extent compared with identical concentrations of eugenol.

TABLE 4

| | Concentration of eugenol [µm] | | | | | | |
|---|---|---|---|---|---|---|---|
| | 0 | 0.6 | 6 | 30 | 45 | 60 | 90 | 120 |
| Sporulation [%] | 100 | 100 | 100 | 100 | 100 | 100 | 10 | 10 |

| | Concentration of farnesol [µm] | | | | | | |
|---|---|---|---|---|---|---|---|
| | 0 | 0.5 | 5 | 25 | 35 | 50 | 70 | 90 |
| Sporulation [%] | 100 | 100 | 100 | 100 | 60 | 80 | 50 | 40 |

| Ingredients | Quantity |
|---|---|
| Methylhydroxyethyl cellulose (300 mPas in 2% aqueous solution, methoxyl content 26%) | 500 g |
| PVAcetate redispersion powder | 350 g |
| Kaolin | 60 g |
| Cellulose powder | 50 g |
| Addition product von 6 mol ethylene oxide onto 1 mol nonyl phenol | 10 g |
| Commercial preservative (based on isothiazoline derivative) | 8 g |
| Eugenol | 0.1 g |

| Ingredients | Quantity |
|---|---|
| Methylhydroxyethyl cellulose (5000 mPas in 2% aqueous solution, methoxyl content 19%) | 680 g |
| Carboxylmethyl starch (DS 0.22) | 300 g |
| Addition product von 4 mol ethylene oxide onto 1 mol fatty alcohol | 15 g |
| Commercial preservative (based on isothiazoline derivative) | 10 g |
| Eugenol | 0.1 g |

| Ingredients | Quantity |
|---|---|
| Commercial polyvinyl acetate dispersions (50% solids content) | 500 g |
| Water | 200 g |
| Methylhydroxyethyl cellulose (3000 mPas in 2% aqueous solution) | 20 g |
| Commercial preservative | 10 g |
| Eugenol | 0.1 g |

The mixtures obtained were made into pastes by stirring with water in a ratio of 1:20 (2) or 1:25 (3) or 1:1 (4) and used to hang commercially available wallpapers on walls

| Liquid detergent | |
|---|---|
| Raw material | Quantity in % by weight |
| $C_{12-18}$ fatty alcohol + 7EO (Dehydol LT 7, Cognis) | 15 |
| $C_{12-14}$ fatty alcohol + 2EO sulfate, sodium salt (Texapon N 70, Cognis) | 7 |
| $C_{8-18}$ fatty acid cut (coconut oil fatty acid, Edenor K12-18, Cognis) | 8 |
| Sodium citrate | 1.5 |
| Enzymes | + |
| Dye | + |
| Perfume | + |
| Eugenol | 0.2 |
| Water | to 100 |

What is claimed:

1. An adhesive comprising at least one of eugenol and one or more derivatives thereof, wherein the concentration of the eugenol and/or each of the one or more derivatives thereof in the adhesive is 0.000001% to 0.001% by weight.

2. The adhesive of claim 1 wherein the adhesive is water-based.

3. The adhesive of claim 1 wherein the adhesive is an adhesive for hanging wallpaper and wall covering materials.

4. A sealing compound comprising at least one of eugenol and one or more derivatives thereof, wherein the concentration of the eugenol and/or each of the one or more derivatives thereof in the sealing compound is 0.000001% to 0.001% by weight.

5. The sealing compound of claim 4 wherein the sealing compound is a jointing compound.

6. The adhesive of claim 1 wherein the concentration of each of the eugenol and/or the one or more derivatives thereof in the adhesive is 0.00001% to 0.0001% by weight.

7. The adhesive of claim 1 wherein the concentration of each of the eugenol and/or the one or more derivatives thereof in the adhesive is 0.0001% to 0.001% by weight.

8. The adhesive of claim 3 comprising an aqueous solution of a hydrocolloid.

9. The adhesive of claim 8 wherein the hydrocolloid is methylcellulose, methylhydroxypropyl cellulose, a water-soluble starch derivative, or polyvinyl acetate.

10. The sealing compound of claim 4 wherein the concentration of each of the eugenol and/or the one or more derivatives thereof in the sealing compound is 0.00001% to 0.0001% by weight.

11. The sealing compound of claim 4 wherein the concentration of each of the eugenol and/or the one or more derivatives thereof in the sealing compound is 0.0001% to 0.001% weight.

12. The sealing compound of claim 4 comprising a silicone, a urethane, or an acrylate.

13. The sealing compound of claim 4 comprising an aqueous solvent or an organic solvent.

14. The sealing compound of claim 4 comprising a rubber-like polymer.

* * * * *

UNITED STATES PATENT AND TRADEMARK OFFICE
CERTIFICATE OF CORRECTION

PATENT NO. : 7,557,145 B2
APPLICATION NO. : 11/305380
DATED : July 7, 2009
INVENTOR(S) : Mirko Weide et al.

It is certified that error appears in the above-identified patent and that said Letters Patent is hereby corrected as shown below:

Title Page,
Item (30) Foreign Application Priority Data:
After "103 27 136" insert -- .8 --.
After "103 27 137" insert -- .6 --.

Title Page,
Item (56) References Cited:
OTHER PUBLICATIONS
Page 2, column 2, "Database Biosis Accession No. PREV198579104006;" reference,
line 10, delete "XP00297855." and insert -- XP002297855. --.
Page 2, column 2, "Cajkovac et al." reference, delete "790-792]." and
insert -- 790-791]. --.

Column 1,
Line 63, after "surfaces" insert -- . --.

Column 3,
Line 63, delete "Stammsanunlung" and insert -- Stammsammlung --.

Column 4,
Line 3, delete "fingi." and insert -- fungi. --.
Line 11, after "Chaetonium" insert -- . --.

Column 9,
Line 61, delete "$C_{12-1}8$" and insert -- $C_{12-18}$ --.

Column 11,
Line 63, delete "anination" and insert -- amination --.

Column 12,
Line 63, delete "Cogris" and insert -- Cognis --.

Signed and Sealed this

Twelfth Day of October, 2010

David J. Kappos
*Director of the United States Patent and Trademark Office*

Column 14,
Line 2, delete "polyquatemium-7" and insert -- polyquaternium-7 --.
Line 3, delete "polyquatemium-10" and insert -- polyquaternium-10 --.
Line 4, delete "polyquatemium-4" and insert -- polyquaternium-4 --.
Line 28, delete "quatemium-80," and insert -- quaternium-80, --.
Lines 33-41, delete

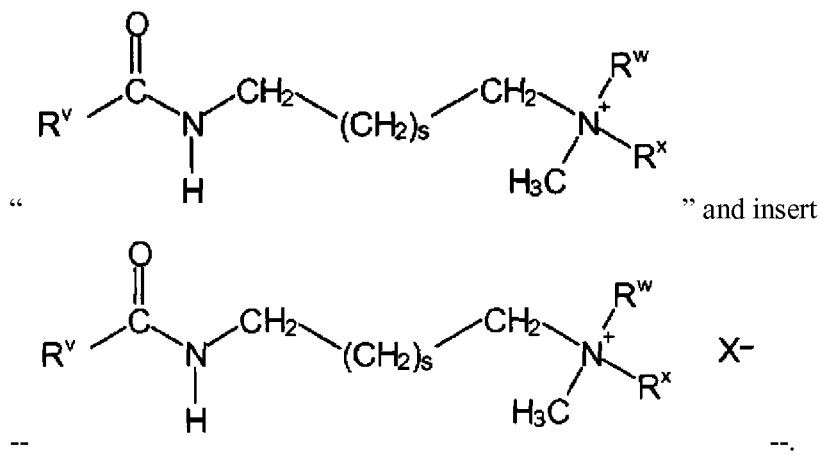

" and insert

--                                                                       --.

Column 15,
Line 2, delete "NaMSi$_x$O$_{2+1}$·H$_2$O," and insert -- NaMSi$_x$O$_{2x+1}$·H$_2$O, --.

Column 20,
Lines 3-4, delete "4-(2-oxo-3-bomylidenemethyl)-benzene" and insert
-- 4-(2-oxo-3-bornylidenemethyl)-benzene --.
Lines 4-5, delete "2-methyl-5-(2-oxo-3-bomylidene)-sulfonic" and insert
-- 2-methyl-5-(2-oxo-3-bornylidene)-sulfonic --.

Column 23,
Line 30, delete "105 CFU/ml" and insert -- 10$^5$ CFU/ml --.

Column 24,
Line 28, insert -- Example 4: --.
Line 42, insert -- Example 5: --.
Line 54, insert -- Example 6: --.
Line 67, after "walls" insert -- . --.

Column 25,
Line 2, insert -- Example 7: --.